(12) United States Patent
Brown et al.

(10) Patent No.: US 8,322,200 B2
(45) Date of Patent: Dec. 4, 2012

(54) METHOD FOR CERTIFYING COMPOSITION AND PROPERTY VARIABLES OF MANUFACTURED PETROLEUM PRODUCTS

(75) Inventors: James M. Brown, Flemington, NJ (US); Tian Chong Lau, Whitby (CA)

(73) Assignee: ExxonMobil Research and Engineering Company, Annandale, NJ (US)

(\*) Notice: Subject to any disclaimer, the term of this patent is extended or adjusted under 35 U.S.C. 154(b) by 483 days.

(21) Appl. No.: 12/285,176

(22) Filed: Sep. 30, 2008

(65) Prior Publication Data

US 2009/0158824 A1 Jun. 25, 2009

Related U.S. Application Data

(60) Provisional application No. 61/008,585, filed on Dec. 21, 2007.

(51) Int. Cl.
*G01N 33/22* (2006.01)
(52) U.S. Cl. ...................................................... 73/64.56
(58) Field of Classification Search ........................ None
See application file for complete search history.

(56) References Cited

U.S. PATENT DOCUMENTS 6,100,975 A * 8/2000 Smith et al. ............... 356/301
2006/0278304 A1 * 12/2006 Mattingly et al. ............ 141/100

OTHER PUBLICATIONS

International Search Report, PCT/US2008/13819, mailed Feb. 25, 2009.
Written Opinion, PCT/US2008/13819, mailed Feb. 25, 2009.

\* cited by examiner

*Primary Examiner* — Hezron E Williams
*Assistant Examiner* — Mark A Shabman
(74) *Attorney, Agent, or Firm* — W. Robinson H. Clark; Glenn T. Barrett

(57) ABSTRACT

The present invention uses the one or more on-line process analyzers that monitor the manufacture of petroleum products, such as gasoline or diesel fuel, to analyze and/or certify that the manufactured product meets regulatory and/or contractual requirements. The analysis is performed by re-introducing a manually or automatically collected sample that is representative of the manufactured product back into the one or more process analyzers. The results obtained for the representative sample from the on-line process analyzers are then used to represent the quality of the manufactured batch of petroleum material to certify that the manufactured batch meets regulatory, specification and/or contractual requirements.

6 Claims, 1 Drawing Sheet

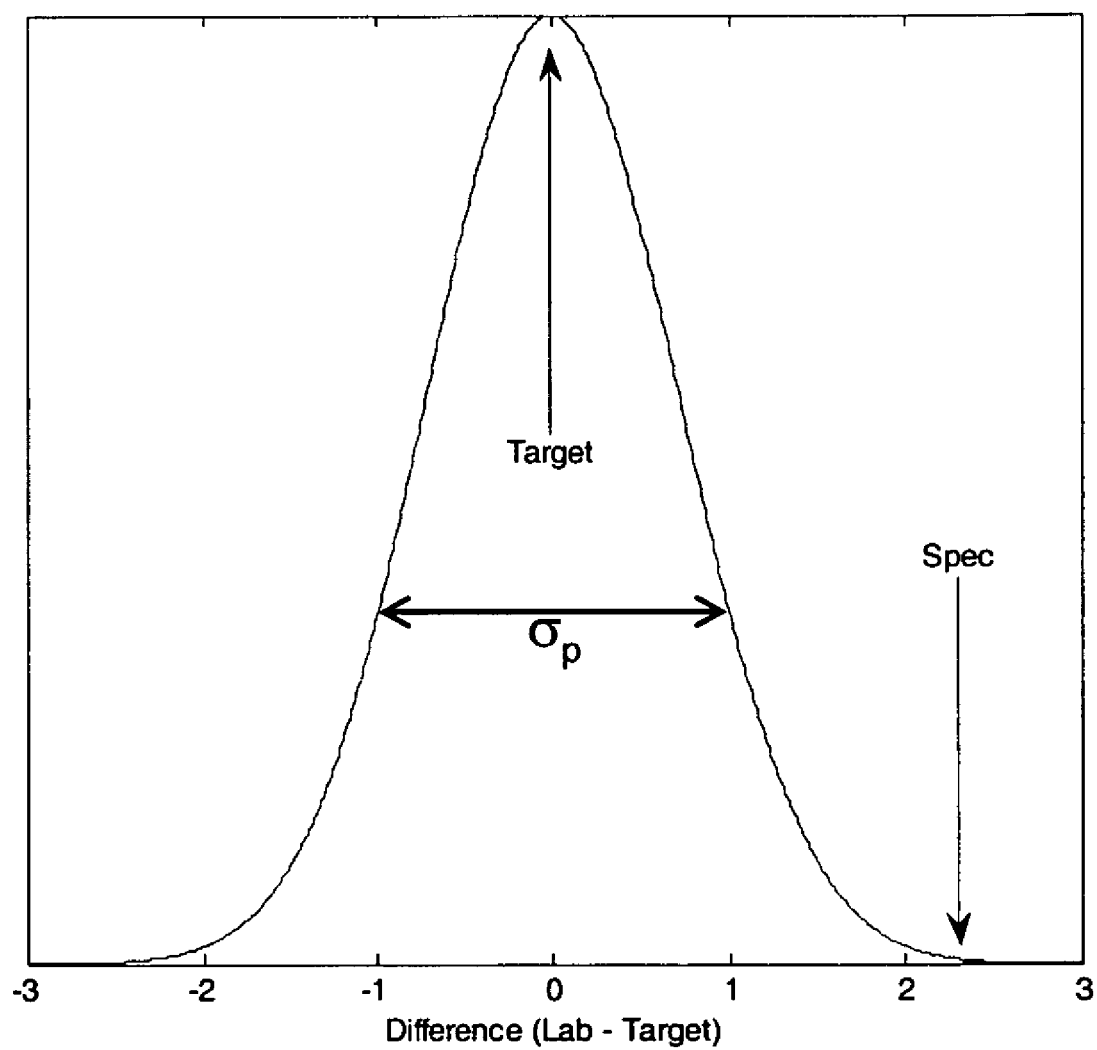

METHOD FOR CERTIFYING COMPOSITION AND PROPERTY VARIABLES OF MANUFACTURED PETROLEUM PRODUCTS

CROSS REFERENCE TO RELATED APPLICATIONS

This application relates to and claims priority to U.S. Provisional Patent Application No. 61/008,585, entitled "Method for Certifying Composition and Property Variables of Manufactured Petroleum Products," filed on Dec. 21, 2007.

BACKGROUND OF THE INVENTION

1. Field of the Invention

The invention relates to a method for analyzing and certifying the composition and/or properties of manufactured petroleum products.

2. Description of Related Art

Many petroleum refinery products such as gasoline and diesel fuel are typically manufactured. For one example, several petroleum refinery streams that differ in composition and properties may be blended to form a petroleum fuel product. For another example, the petroleum product may be subjected to treatments such as sulfur removal or additive injection. In most instances the final product must meet regulatory and/or contractual requirements. Typically, the overall objective of the manufacturing process is to produce a regulatory or contractually compliant product, while minimizing the overall cost of production.

In many manufacturing processes, the composition and properties of the components, such as the blend component streams, are used as input to a set of blending equations (a.k.a., a blending model) to estimate a blend recipe that ensures the blended or manufactured product meets targeted composition or property values. The actual composition and properties of the blended product however do not always agree with that calculated from the blend recipe. Various reasons for this discrepancy exist including but not limited to: errors in the composition/property estimates for the blend components; errors in the blending model; errors in the blending flow control; random and systematic errors in the measurement systems used to control and certify the final blend properties.

To assist in the manufacture or blending of petroleum refinery products, a Flow Proportioned Average Property Value (FPAPV) for the aggregated manufactured product is often calculated. The FPAPV values are based on the integration of process analyzer values and the measured flow of the manufactured product that make up the aggregated volume of the manufactured product (using for example ASTM D6624). The FPAPV is typically calculated for each compositional and property parameter.

FPAPV values are, in conjunction with the instantaneous (on-line process) analyzer values, continuously compared to targets, and the relative component ratio or other key manufacturing process parameters can be adjusted accordingly. These calculated values, however, are not currently acceptable for certifying that a product meets EPA regulatory specifications, and, may not be acceptable to some customers as the supplier certified value to deem the product meeting specification requirements.

Instead, when product is blended to tank or otherwise manufactured, generally accepted practice is to take samples of the product from the tank (typically top, middle and bottom) and analyze the samples in a laboratory (i.e., off-line instrumentation). Usually the samples are collected upon completion of the manufacture. The analysis is typically performed using EPA designated methods and/or contractually specified methods to determine if product specification and/or EPA requirements are met. For instances where the manufactured product is blended directly to pipeline, barge, ship or tank car, ASTM D 4177 (used in conjunction with D 5482 for volatility measurement) is used to collect a composite sample that is representative of the blend. For regulatory and contractual compliance, this composite sample is analyzed in a laboratory using EPA designated or contractually specified methods with off-line instrumentation for final certification purposes upon completion of manufacture. The measurement methodology used in the off-line instrumentation is usually different from that used with the on-line process analyzer during the manufacture of the petroleum refinery product.

In many manufacturing processes of petroleum refinery products, the producer establishes a manufacture or blending target for each composition or property variable for which there is a regulatory or contractual specification. In order to control the risk (probability) that the final certification measurement will show the product to be off-specification, (thereby incurring business penalties associated with re-work, product downgrade, or missed shipment), it is generally necessary to adjust manufacturing or blend targets farther from the regulatory or specification values, on the compliant side. These adjusted targets account for the overall variability of the planning, manufacturing, sampling, and testing processes. Meeting these adjusted targets generally requires use of higher proportions of more expensive blend or manufacturing components, thereby increasing the manufactured cost of the petroleum product.

A significant portion of the overall variability described in the process can be attributed to the variation of the disagreement (difference) between on-line analyzer generated values (instantaneous and FPAPV) that are used to control the manufacturing process, versus the final laboratory (off-line) certification results. The variability of this difference is quantified by the cross-method reproducibility (reference ASTM D 6708) between the on-line process analyzers and off-line laboratory methods. Blend or manufacturing targets are adjusted farther away from the regulatory and contractual specification values to account for the cross-method reproducibility between the on-line process analyzers and off-line laboratory methods. The difference between the manufacture target and the specification limit is often referred to as the manufacturing offset. In general, the cost of manufacture of the product is directly proportional to the magnitude of the manufacturing offset. Hence, there is a strong economic incentive for the manufacturer to minimize such offsets.

To reduce the manufacturing offset (and hence the associated cost) of manufacturing petroleum products that are compliant with contractual and/or regulatory specifications, there is a need for a method that minimizes the variability in the blending and/or manufacturing of petroleum refinery products. It would be desirable to have a method of certifying the composition or properties of a manufactured petroleum product that reduces or eliminates the cross-method reproducibility contribution towards the manufacturing offset.

BRIEF DESCRIPTION OF THE DRAWINGS

The following drawings are for illustrative purposes only and are not intended to limit the scope of the present invention in any way:

FIG. 1 illustrates a graph depicting the probability (risk) that blends made to that target will be measured as non-compliant to regulatory or specification requirement by the laboratory.

SUMMARY OF THE INVENTION

A method and apparatus is provided whereby a representative sample of a manufactured petroleum refinery product is analyzed and certified upon completion of product manufacture using, and preferably only using, on-line process analyzer(s) used to monitor the manufacture of the petrochemical product. The representative sample, obtained for example either by the manual compositing of samples taken from the process during manufacture, or from a tank upon completion of manufacture, or by an automatic composite sampler, is re-introduced into the on-line process analyzer(s) for analysis, with the on-line process analyzer(s) operating strictly as a product certification analytical system. Results of the analysis are used to demonstrate regulatory or specification conformance.

As used herein, petroleum refinery product (or alternatively petroleum product) includes hydrocarbons, gasoline, diesel, vacuum gas oil, and petrochemical streams and products.

By using the same process analyzers to both monitor and also certify manufactured petroleum product, manufacture offset from specification can be reduced. The measurement portion of the total manufacturing offset is based on analyzer precision as opposed to cross-method reproducibility, which involves an additional off-line measurement system. This reduction in manufacturing offset directly reduces the cost of the blended or manufactured product.

Setting the targets based on analyzer precision allows for blend or manufacturing targets to be set closer to the regulatory and contractual specification values than would feasible using laboratory certification. Under the methods provided by the invention the manufacturing or blending offset can be significantly reduced while maintaining the same risk of non-conformance.

DETAILED DESCRIPTION

Overview

The present invention uses one or more of the on-line process analyzers (sometimes referred to simply as "process analyzer") used to monitor the manufacture of petroleum products, such as gasoline or diesel fuel, to analyze and/or certify the final manufactured product. The analysis of the manufactured product is performed to ensure that the product meets regulatory and/or contractual requirements.

The analysis is performed by re-introducing a manually or automatically collected sample that is representative of the manufactured product back into one or more of the process analyzers upon completion of the manufacturing process. The results obtained for the representative sample from the on-line process analyzers are then used to represent the quality of the batch of manufactured petroleum product and to certify that the manufactured batch meets regulatory, specification or contractual requirements.

The on-line process analyzers preferably utilize measurement methods that are either EPA designated regulatory methods, or other types of measurement methods that have been deemed qualified by regulatory agencies or by the recipients of the product as acceptable through demonstrated performance criteria (e.g.: EPA's Performance Based Criteria for sulfur measurements in Ultra Low Sulfur Diesel).

On-Line Process Analyzers

During the manufacture of many petroleum products, analytical data from one or more on-line process analyzers is collected. A process analyzer is a piece of analytical instrumentation or equipment (and supporting ancillary equipment) that measures a compositional component or property of a petroleum product. An on-line process analyzer is a process analyzer that is structured to receive a live-feed of the manufactured petroleum product during the manufacturing process. The structure permits the real time analysis of the manufacturing process during the manufacture. This analysis is typically performed at a predetermined frequency. The on-line analysis by the process analyzers is essentially done in real time within a blend or during manufacture.

The real time data obtained by the on-line process analyzer or analyzers is used as input to an automatic control program or to process operators to make adjustments to key manufacturing process operating parameters. That is, adjustments to the manufacturing process such as blend make-up, recipes, and targets for key operating parameter changes are made in response to the data from the on-line process analyzers. The changes are designed to drive the measured property value to an economically optimal target value using an economically optimal admixture of components, while ensuring compliance to regulatory and contractual requirements and specifications. Examples of key manufacturing process operating parameters can be (but not limited to) the relative ratios of component flows to a blending facility, the operating temperature or pressure of a treatment facility (e.g., sulfur removal), or the flow of chemical additives.

More than one on-line process analyzer may be used for a specific manufacturing process, and throughout the specification any reference to an on-line process analyzer means one or more on-line process analyzers. No particular process analyzers are required for implementing the method of the current invention. Process analyzers known and used by those skilled in the art can be used as the process analyzer for analyzing the representative sample. The specific choice of process analyzers will depend on the specific regulatory or contractual requirements for the manufactured petroleum product.

Specifically, the on-line process analyzers used in a manufacture will depend on the specific composition or property of interest. If there are targets for more than one property or component, it may be necessary to have more than one process analyzer. Non-limiting examples of process analyzers are discussed in more detail below and include vapor pressure analyzers and octane analyzers.

Representative Sample of the Manufactured Petroleum Product

A representative sample of the manufactured product is prepared. The representative sample can be collected or obtained during the manufacturing process or after the manufacturing process. The representative sample can be obtained in a variety of ways; the method of collection is chosen so that the sample accurately reflects the properties or composition of the manufactured product. In one embodiment the representative sample is a manually composited sample. For another example, the representative sample is collected by an automatic composite sampler during the manufacture of the batch. For another example, the representative sample can be prepared from multiple samples taken from the manufacturing process during the manufacture of the batch, or at various spatial locations of the manufactured product containment facility (such as top, middle, and bottom of a product tank). This representative sample is preferably collected upon completion of the batch.

Analysis of the Representative Sample

Once collected or obtained, one or more aliquots of the representative sample are re-introduced into the same process analyzer or process analyzers upon completion of the manufacture of the petroleum product. When reintroduced, the process analyzer measures the same composition or property values of the representative sample that was measured by the on-line process analyzer during the manufacturing process. Again, the specific properties measured by the on-line process analyzer are preferably chosen to be those required to certify the final product.

By using the same on-line analyzers to both monitor the manufacturing process during product manufacture and analyze a representative sample of the manufactured product upon completion of the manufacture process for product representation and certification purposes, the present invention allows for more accurate and economical manufacture of on-specification product. Specifically, the variation from another (off-line) measurement system is removed in the final product inspection process. As a result, the blend targets can be set closer to the regulatory and contractual specifications, reducing cost of production.

While not bound by theory, reintroducing the composite sample into the process analyzers to obtain official certification values permits the reduction of the manufacturing offset, and thereby the manufacturing cost. More particularly, in setting the blend targets for each composition and property parameter, where the final judgment of product conformance is based on the laboratory analyses on samples taken from the finished product tank or the automatic composite sampler, the refiner must take into account at least two principal factors: 1) the cross (between)-method reproducibility between the on-line analyzers used for control and/or to calculate the FPAPV, versus the final certification test method used in the lab; and 2) the capability of the control program to achieve the desired target. For each parameter, p, the difference between the analyzer result, or, FPAPV and the corresponding result measured in the laboratory on the material intended for certification or compliance demonstration, can generally be adequately modeled by the Normal distribution with a standard deviation $\sigma_p$.

In general, a properly tuned blend program can always achieve the desired blend target if the blending components requested by the control program are available. Therefore, assuming the capability of the blend control program to achieve blend target is at or near 100% (i.e., is perfect or near perfect), it can be seen that unless $\sigma_p$ is zero (which is theoretically unachievable), the target still needs to be set with an offset on the conforming side of the specification in order to ensure that there is an acceptably small probability (risk) that blends made to that target will be measured as non-compliant to regulatory or specification requirement by the laboratory. FIG. 1 illustrates this concept, using a maximum specification (which similarly applies to a minimum specification). Assuming the blend control program can achieve the desired blend target 100% of the time, when a blend is made to a target 2.33$\sigma_p$ below the specification, the lab certification value will exceed the specification about 1 time in 100 over the course of many productions. In other words, if it is desired to control the risk of the lab certification value exceeding the specification to 1%, even with a perfect blending control program, the blend target can not be set closer to the specification than 2.33$\sigma_p$. Therefore, for a given desired risk of laboratory result failing to meet specification, $\sigma_p$ directly impacts the magnitude of offset between the specification limit and the blend target in that the larger the $\sigma_p$, the larger the offset needs to be to maintain the same risk.

In practice $\sigma_p$ is the combination of three terms: $\sigma_{p\text{-relative bias between analyzer and lab}}$; $\sigma_{p\text{-analyzer measurement}}$; and $\sigma_{p\text{-lab measurement}}$. $\sigma_{p\text{-relative bias between analyzer and lab}}$ is the standard deviation of the systemic differences between the on-line process analyzer and the laboratory test methods throughout the manufacturing envelope over time. $\sigma_{p\text{-analyzer measurement}}$ is the standard deviation of the random variation of the on-line process analyzer over time, while $\sigma_{p\text{-lab measurement}}$ is the standard deviation of the random variation of the laboratory measurements.

$$\sigma_p = \sqrt{\sigma^2_{p\text{-relativebias}} + \sigma^2_{p\text{-ananlyzermeasurement}} + \sigma^2_{p\text{-labmeasurement}}}$$

In the inventive method and apparatus $\sigma_{p\text{-relative bias between analyzer and lab}}$, and $\sigma_{p\text{-lab measurement}}$ are removed from the final inspection/certification process because the same analyzer system is used to obtain the blend FPAPV and the representative sample certification values. This removal leaves only the $\sigma_{p\text{-analyzer measurement}}$ and the ability for the control program to ensure the FPAPV achieves the target value as the two sources of variation. With a properly tuned control program, and proper blend component inventory management, the dominant source of manufacturing variation will be only the $\sigma_{p\text{-analyzer measurement}}$ component since the control program will drive the FPAPV to the target value at the completion of the blend.

Illustrative Process Analyzers

At least two general classes of analyzers may be used to implement the current invention. Other classes may also be used; but these general classes represent analyzers that are commonly used by those in the art.

The first class of analyzers includes those that are designed to directly measure the composition or property parameter. This class of analyzers includes, but is not limited to, RVP analyzers, physical distillation analyzers such as the PAC single boiling point or full boiling curve analyzers, and gas chromatographic analyzers for measuring benzene, aromatics or oxygenates.

The second class of analyzers includes those that use multivariate chemometric models to relate the measured analyzer data (typically a spectrum) to the composition or property parameters of interest. This class of analyzers includes, but is not limited to, FTIR analyzers, dispersive NIR analyzers and Raman analyzers.

Currently, the EPA has not promulgated a universal Fuels PBMS rule (except for sulfur measurement in ULSD). Preferably, the method of the current invention is qualified with typical analytical methodology known to those in the art.

For example, qualifying the use of a process analyzer for final analysis or certification of the composite sample would preferably, but not necessarily include: (1) a demonstration that the analytical method accurately measures the property of interest, either relative to a designated referee test method, or relative to a suite of standard reference materials with a specified protocol for determination of the reference values; and/or (2) a demonstration that the analytical method is sufficiently precise, relative to a specific precision estimate such as test method reproducibility, repeatability, or some combination of both. Such demonstrations are known to those in the art and may be made following methodology described in various ASTM standards.

In one embodiment, the qualification of the first class of analyzer (i.e., those that are designed to directly measure the composition or property parameter) as accurate and reliable or as a PBMS acceptable method includes three steps. The three steps, detailed below, entail a correlation, initial validation and continual validations.

Correlation: As described in ASTM D7324, in the correlation step, a minimum of thirty (30) samples that span the range of production are measured using both the analyzer and the corresponding laboratory certification method. A correlation equation is developed to relate the analyzer results to the lab certification results, preferably employing the statistical methodology of ASTM D6708. Applying the correlation to the analyzer result produces a predicted lab certification (designated method) result.

Initial Validation: Once the correlation is developed, it is validated using a separate set of preferably at least thirty (30) samples which span the range of blended products. This initial validation is conducted using the statistical methodology of ASTM D6708 as described in ASTM D3764. The correlation equation is then used in the process analyzer to convert the raw analyzer results into predicted lab certification (designated method) results.

Continual Validation: Once the analyzer is in use for product certification, a periodic validation is conducted using the line sample procedure in ASTM D3764. The sample is withdrawn from the blend process while simultaneously, the analyzer result is recorded. The sample is analyzed using the lab certification (designated) method, and the difference between the lab certification value and the predicted lab certification value (calculated by applying the correlation equation to the analyzer results) are control charted following the procedures of ASTM D6299 to ensure that the bias between the predicted analyzer result and lab certification values are acceptably small. In addition, a Quality Control (QC) sample will periodically be introduced into the on-line analyzer, and the predicted lab certification value for the QC sample will be controlled charted using the procedures of ASTM D6299. The QC results are used to demonstrate that the site precision for the on-line analyzer is acceptable. The QC sample will typically be a sample of blended product that is stored for this purpose.

Some typical steps to qualify the second class of analyzer, namely, those that use multivariate chemometric models to relate the measured analyzer data (typically a spectrum) to the composition or property parameters of interest, as accurate and reliable or as PBMS acceptable methods may also in one embodiment include three steps. Again, the three steps, detailed below, entail a correlation, initial validation and continual validation.

Correlation: In the correlation step, a set of calibration samples that span the range of production are measured using both the analyzer and the corresponding laboratory certification method. A multivariate calibration model is developed to relate the analyzer data to the lab certification results, preferably employing the statistical methodology of ASTM E1655. Applying the multivariate model to the analyzer data produces a predicted lab certification (designated method) result. The number of samples used in developing the calibration must be at least six (6) times the number of variables used in the multivariate model.

Initial Validation: Once the multivariate model is developed, it is validated using a separate set of samples which span the range of blended products. This initial validation is conducted using the statistical methodology of ASTM D6708 as described in ASTM E1655 and D6122. The number of samples used in validating the calibration is at least 4 times the number of variables used in the multivariate model. The multivariate model is then used on the process analyzer to convert the raw analyzer data into predicted lab certification (designated method) results.

Continual Validation: Once the analyzer is in use for product certification, a periodic validation is preferably conducted using the line sample procedure in ASTM D6122. The sample is withdrawn from the blend process while simultaneously, the analyzer result is recorded. The sample is analyzed using the lab certification (designated) method, and the difference between the lab certification value and the predicted lab certification value (calculated by applying the multivariate model to the analyzer data) are control charted following the procedures of ASTM D6299 to ensure that the bias between the predicted analyzer result and lab certification values are acceptably small. In addition, QC samples are periodically introduced into the on-line analyzer, and the predicted lab certification value for the QC sample will be controlled charted using the procedures of ASTM D6299. The QC results are used to demonstrate that the site precision for the on-line analyzer is acceptable. The QC sample will typically be a sample of blended product that is stored for this purpose.

Equipping an On-Line Process Analyzer

No one particular equipment setup is required to analyze the representative sample on the one or more on-line analyzers and the specific equipment will depend on the operations of the specific analyzer being used. Generally, on-line process analyzers will need to be equipped with piping and/or ports, and/or motive force necessary to manually or automatically introduce a representative sample of the manufactured batch back into the on-line process analyzer or analyzers for analysis.

In one embodiment, to execute the procedures in the previously mentioned ASTM practices, the process analyzer is equipped with sample ports by which line samples are withdrawn and tested in accordance with D3764 or D6122. In another embodiment, a flow-proportional automated composite sampling system meeting the functional requirement of ASTM D4177 is installed.

Examples of the motive force to re-introduce the representative sample from the manufactured batch for re-analysis by the on-line process analyzer include, but are not limited to any of the following: a mechanical pump; piston/cylinder assembly (e.g., Welker cylinders) where the composite sample to be introduced into the analyzer system is stored in one end of a cylinder, and pushed into the analyzer system by application of a pressurized gas into the other end of the cylinder, thus pushing the piston onto the stored material and causing flow of the material into the analyzer system; and a pressurized vessel where a gas inert to the stored liquid material is used to push the liquid material into the process analyzer system.

Optional equipment includes manufacture material extraction, storage and mixing, and re-injection facilities. The manufactured material collected is to be used for analyzer system quality control purposes by re-introducing the same material back into the process analyzer system for the purpose of obtaining an analysis by the on-line process analyzer or analyzers. Such equipment permits the capture of an amount of manufactured product that is suitably mixed (i.e., representative sample) and stored. Optionally, additional QC and Check Standard storage tanks are provided where the QC and check standard material are externally prepared and connected to the re-injection facility, allowing QC and/or check standards to be introduced for analysis as needed.

Alternatives

There will be various modifications, adjustments, and applications of the disclosed invention that will be apparent to those of skill in the art, and the present application is intended to cover such embodiments. Accordingly, while the present invention has been described in the context of certain preferred embodiments, it is intended that the full scope of these be measured by reference to the scope of the following claims.

What is claimed is:

1. A method for analyzing at least one of a target composition and target properties of a petroleum product manufactured by blending together several petroleum streams which differ in composition and/or properties, comprising:

monitoring at least one of the target composition and target properties of the manufactured petroleum product during the blending of the manufactured petroleum product, wherein the monitoring includes using at least one process analyzer to monitor at least one of the target composition and target properties;

obtaining a representative sample of the blended petroleum product;

analyzing the representative sample for at least one of the target composition and target properties of the representative sample of the blended petroleum product by introducing the representative sample into the same at least one process analyzer used to monitor the at least one of the target composition and the target properties of the blended petroleum product during the manufacture of the blended petroleum product.

2. The method of claim 1 wherein the representative sample is obtained by an automatic composite sampler during the blending of the petroleum product.

3. The method of claim 1 wherein the representative sample is prepared from multiple samples taken from the product during the blending of the petroleum product.

4. The method of claim 1 wherein the representative sample is prepared from multiple samples taken from various spatial locations of the blended product containment facility.

5. The method according to claim 1, further comprising:
certifying the blended petroleum product based upon the analyzing of the representative sample.

6. The method of claim 5, wherein the certifying of the blended petroleum product includes comparing the analysis of the representative sample to a manufacture target.

* * * * *